(12) United States Patent
Franzen

(10) Patent No.: US 8,581,179 B2
(45) Date of Patent: Nov. 12, 2013

(54) PROTEIN SEQUENCING WITH MALDI MASS SPECTROMETRY

(75) Inventor: Jochen Franzen, Bremen (DE)

(73) Assignee: Bruker Daltonik GmbH, Bremen (DE)

( * ) Notice: Subject to any disclaimer, the term of this patent is extended or adjusted under 35 U.S.C. 154(b) by 254 days.

(21) Appl. No.: 12/708,010

(22) Filed: Feb. 18, 2010

(65) Prior Publication Data

US 2010/0237238 A1 Sep. 23, 2010

(30) Foreign Application Priority Data

Mar. 18, 2009 (DE) .................... 10 2009 013 653

(51) Int. Cl.
*H01J 49/40* (2006.01)
*H01J 49/04* (2006.01)

(52) U.S. Cl.
USPC ........................................ 250/282; 250/286

(58) Field of Classification Search
USPC .................. 250/281, 282, 283, 287, 288, 286
See application file for complete search history.

(56) References Cited

U.S. PATENT DOCUMENTS

| | | | |
|---|---|---|---|
| 5,087,814 A * | 2/1992 | Ichimura et al. | 250/287 |
| 5,202,561 A * | 4/1993 | Giessmann et al. | 250/281 |
| 5,654,545 A | 8/1997 | Holle et al. | |
| 5,777,326 A * | 7/1998 | Rockwood et al. | 250/287 |
| 6,300,627 B1 | 10/2001 | Koster et al. | |
| 6,627,879 B2 * | 9/2003 | Reilly et al. | 250/287 |
| 7,180,058 B1 * | 2/2007 | Izgarian | 250/288 |
| 7,235,781 B2 * | 6/2007 | Haase et al. | 250/288 |
| 7,396,686 B2 | 7/2008 | Suckau et al. | |
| 7,928,361 B1 * | 4/2011 | Whitehouse et al. | 250/281 |
| 7,989,759 B2 * | 8/2011 | Holle | 250/287 |
| 7,989,762 B2 * | 8/2011 | Holle et al. | 250/288 |
| 2002/0175292 A1 * | 11/2002 | Whitehouse et al. | 250/394 |
| 2003/0001089 A1 * | 1/2003 | Reilly et al. | 250/287 |

(Continued)

FOREIGN PATENT DOCUMENTS

| | | |
|---|---|---|
| DE | 29 25 451 A1 | 1/1981 |
| DE | 100 37 859 A1 | 3/2002 |

(Continued)

OTHER PUBLICATIONS

Demeure, et al., "Rational Selection of the Optimum MALDI Matrix for Top-Down Proteomics by In-Source Decay", Analytical Chemistry, vol. 79, No. 22, Nov. 15, 2007, pp. 8678-8685, American Chemical Society.*

*Primary Examiner* — David A Vanore
*Assistant Examiner* — Wyatt Stoffa
(74) *Attorney, Agent, or Firm* — Robic, LLP

(57) ABSTRACT

In a mass spectrometer, sample ions are produced by using matrix assisted laser desorption with a matrix substance that supports spontaneous, non-ergodic ISD fragmentation and a laser light source with nanosecond light pulses and a multiple spot beam profile. A plurality of individual time-of-flight spectra are recorded from the resulting ions in such a way that amplification of ion signals in the mass spectrometer detector is initially reduced so that only ions with masses near a mass range limit are initially recorded. During the repeated acquisitions of the individual time-of-flight spectra, both the detector amplification and the mass range limit are increased. By these methods, it is possible to evaluate c and z fragment ions in lower mass ranges and to directly read N-terminal sequences from near terminus up to 80 amino acids and beyond, and C-terminal sequences up to more than 60 amino acids.

13 Claims, 4 Drawing Sheets

(56) References Cited

U.S. PATENT DOCUMENTS

| | | |
|---|---|---|
| 2004/0089804 A1 | 5/2004 | Dantus et al. |
| 2004/0108451 A1* | 6/2004 | Hansen .......................... 250/281 |
| 2005/0092911 A1* | 5/2005 | Hoyes .......................... 250/282 |
| 2006/0071160 A1* | 4/2006 | Haase et al. ................. 250/288 |
| 2006/0097159 A1* | 5/2006 | Herschbein et al. .......... 250/309 |
| 2006/0231769 A1* | 10/2006 | Stresau et al. ................ 250/397 |
| 2008/0156980 A1* | 7/2008 | Rather et al. ................. 250/287 |
| 2008/0191131 A1* | 8/2008 | Hohndorf et al. ............. 250/283 |
| 2008/0272287 A1* | 11/2008 | Vestal .......................... 250/282 |
| 2009/0039282 A1* | 2/2009 | Haase et al. .............. 250/423 R |
| 2009/0095903 A1* | 4/2009 | Holle .......................... 250/287 |
| 2009/0272893 A1* | 11/2009 | Hieftje et al. ................. 250/282 |
| 2009/0294643 A1* | 12/2009 | Steiner .......................... 250/282 |
| 2010/0140466 A1* | 6/2010 | Hartmer ........................ 250/282 |
| 2011/0071764 A1* | 3/2011 | Prather et al. ................... 702/19 |

FOREIGN PATENT DOCUMENTS

| | | |
|---|---|---|
| GB | 2 453 407 A | 4/2009 |
| JP | 60011156 A | 1/1985 |
| JP | 11 213941 | 6/1999 |
| WO | WO 02/071027 A2 | 9/2002 |
| WO | WO 02071027 A2 * | 9/2002 |

* cited by examiner

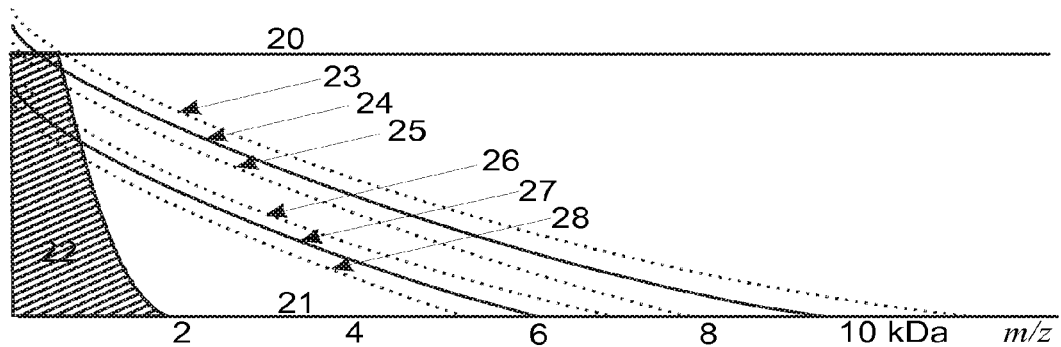
FIG. 4 *(Prior Art)*
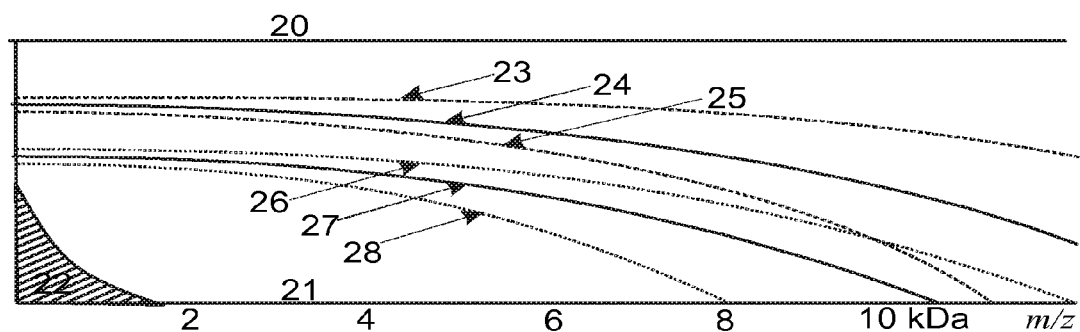
FIG. 5

PROTEIN SEQUENCING WITH MALDI MASS SPECTROMETRY

BACKGROUND

The invention relates to the fast, inexpensive analysis of amino acid sequences of proteins with mass spectrometers that use ionization by matrix assisted laser desorption (MALDI). The standard method for protein sequencing is Edman degradation, which allows a total of between about 30 to 40 amino acids from the N-terminus to be read in suitable machines over a period of around 10 hours, using well-purified protein samples and relatively expensive chemicals. C-terminal amino acids cannot be determined. If the N-terminus is blocked, the method does not work. Since this method is no longer adequate to meet modern demands in terms of cost, speed of analysis and sequencing lengths, automatic Edman sequencers are no longer manufactured. At present, the search is on for methods that operate more quickly, economically and with greater sequencing lengths.

A device (conceivable, although not yet existent) for large-scale protein sequencing capable of a thousand sequence analyses of proteins or split segments with up to 150 amino acids or more per hour would today give a stimulus to many fields of application and open up many new ones. It would permit extensive research into the changes in many different protein types attributable to the evolution of species, and would enormously facilitate the taxonomic classification of species, which is at present carried out on the basis of slow and expensive DNA analyses. In particular, however, it would allow examination of the variations of proteins in the individuals of a species. Our genotype includes hundreds of thousands of SNPs (single nucleotide polymorphisms) that distinguish one person from another. It can be expected that a significant proportion of these polymorphisms are also reflected in variations of the proteins that, in turn, manifest in our phenotype. Genetically conditioned functional changes in many proteins (reduced function, hyperfunction, malfunctions) undoubtedly occur, which can produce altered appearance, altered behavior, altered tolerance of external and internal influences such as foodstuffs, chemicals, pharmaceuticals and many more effects. This could in turn lead to diagnostic methods for the discovery of many abnormalities, including genetically conditioned intolerances and predispositions to disease.

A method that shows high promise as a basis for such automatic sequencing machines and for corresponding assays is the MALDI analysis of protein molecules with randomly generated spontaneous fragmentation, which has become known by the abbreviation "ISD" (in-source decay).

MALDI (ionization by matrix assisted laser desorption) is an important type of ionization for biomolecules, which was developed about 20 years ago by M. Karas and K. Hillenkamp. MALDI ionizes the biomolecules, which are present at high dilution in a matrix substance in predominantly solid samples on sample supports, by firing laser light pulses at them. Each laser light pulse creates a tiny, short-lived cloud of hot plasma containing neutral molecules, and positive and negative ions from a sample.

The ions from the plasma created by each individual laser light pulse are still today preferentially accelerated, after a short delay of several hundred nanoseconds, axially into the flight path of a MALDI time-of-flight mass spectrometer (MALDI-TOF MS) specially designed for this purpose; after transiting the flight path, the ions are passed to a detector that measures the mass-dependent arrival time of the ions and their quantity, and saves the digitized measurements as a time-of-flight spectrum. The delayed extraction (DE) of the ions serves to increase mass resolution for the ions of the expanding plasma plume (see, for instance, A. Holle et al., U.S. Pat. No. 5,654,545 A). Repetition frequencies for the laser light pulses used to be between 20 and 200 hertz; today MALDI-TOF mass spectrometers are available with light pulse frequencies of up to two kilohertz. Nowadays, however, time-of-flight mass spectrometers with orthogonal ion injection (OTOF) are also increasingly being equipped with MALDI ion sources; these record mass spectra at repetition rates of about five kilohertz.

In both types of mass spectrometer, detectors for the ion beams are used that consist of a special secondary electron multiplier (SEM) followed by a transient recorder. The transient recorder contains an extremely fast analog-to-digital converter (ADC), working at between 2 and 4 gigahertz, however, with rather low intensity resolution of usually only 8 bit. The time-of-flight spectra may be up to 200 microseconds long, therefore comprising up to 800,000 measurements. The measurements from several hundreds or thousands of time-of-flight ion spectra acquired in sequence in this way are added to form a sum spectrum. This is subjected to a peak detection process, and the list of time-of-flight peaks is converted by means of a calibration curve into a list of the masses m per number z of elementary charges m/z and their intensities i. By using energy-focusing reflectors and other measures such as delayed extraction (DE) described above, the mass spectra from both types of mass spectrometer can achieve mass resolutions of $R=m/\Delta m=20{,}000$ to $50{,}000$, where $\Delta m$ is the half-height width of the ion peak for the mass m.

The term "mass spectrum" refers, a little ambiguously, either to the list of masses per charge m/z mentioned above with their intensities $i_{m/z}$, or to their graphical representation $i_{m/z}=f(m/z)$ ("line spectrum"), or to the quasi-analog function of the measured values $i_n=f(m/z)$, where n represents the numerator of the measurements in the time-of-flight spectrum.

Whenever the expression "acquisition of a mass spectrum" is used below, it usually means acquiring hundreds or thousands of individual spectra, combining them into a sum spectrum and converting this into a mass spectrum, as described above. This applies equally to mass spectra from molecular ions and to daughter ion spectra.

When the term "mass of the ions", or simply "mass" in connection with ions, is used in the context of mass spectroscopy, it always means the ratio of the mass m to the number z of elementary charges, m/z; in other words, the physical mass m of the ions divided by the dimensionless, absolute number z of the positive or negative elementary charges carried by the ion. The rather unfortunate term "mass-to-charge ratio" is often used for m/z, even though it has the physical dimension of a mass. Since, however, MALDI delivers practically only singly charged ions (z=1), the distinction between "mass" and "mass-to-charge ratio" is in most cases irrelevant here. In this document, the "dalton" (Da) is used as the unit of mass, since this unit is generally used in biochemistry, rather than the statutory, non-coherent SI unit known as the "unified atomic mass unit" with the abbreviation "u" or "amu".

For protein sequencing, it is necessary to record daughter ion spectra (fragment ion spectra) of the protein molecule ions. Two different methods for generating and measuring daughter ions from selected parent ions can be carried out with MALDI:

1) A method using "ergodic" (or "thermal") fragmentation through the decomposition of metastable ions in the mass spectrometer after they have been accelerated in the ion source, a method which primarily creates b and y fragment ions (abbreviated PSD=post-source decomposition, i.e. decomposition after acceleration of the ions). If PSD is to be used in such a way that daughter ion spectra are acquired in a single process, this requires a special and, unfortunately, expensive MALDI-TOF-TOF mass spectrometer equipped with switchable post-acceleration units (see Köster et al., DE 198 56 014 C2; GB 2 344 454 B; U.S. Pat. No. 6,300,627 B1 in this respect).

2) A method of spontaneous, non-ergodic fragmentation of the molecular ions (abbreviated ISD=in-source decay; decomposition before acceleration of the ions in the ion source). The fragmentation of the ions takes place prior to their acceleration, which is delayed, for better mass resolution, by a few hundred nanoseconds (DE); this method primarily yields c and z fragment ions. ISD appears to be particularly suitable for sequence analysis, since it can, in principle, be carried out in simpler and more inexpensive mass spectrometers without post-acceleration units. Within minutes, very good and easily evaluated fragment ion spectra can be generated from protein samples of a purity and quantity approximately equivalent to that of proteins prepared for Edman sequencing, but without the time consumption and material costs of Edman sequencing. In the mass range between about one kilodalton and eight kilodaltons, the c fragment ions yield an outstanding and easily detectable sequence of signals in the mass spectrum, all of which consist roughly of about the same number of ions. The z fragment ions also yield a sequence of signals, each with about the same number of ions, but the mean signal value is lower than that of the c fragment ions by a factor of 5 or 10.

The intensity variations of both sequences of fragment ions lie within a relatively narrow band, extending only by a factor of 1.3 above and below the mean value. All the amino acids thus fragment with about the same probability. Proline is an exception; it has a unique annular structure and therefore, although it may split, nevertheless does not yield two separate fragments.

The various ion detectors all function on the basis of secondary electron multiplication, and their sensitivity therefore falls with the increasing mass. For this reason the mean values of the intensities of the c fragment ions in the mass spectrum also fall with increasing mass, and the possibility of analyzing the c fragment ions in current MALDI-TOF mass spectrometers finishes at a maximum of about 70 amino acids away from the N-terminal end. Starting from the C-terminal end, an evaluation of the z fragment ions can determine a sequence of at most about 50 amino acids.

Unfortunately, the mass spectra that are acquired in this way in currently available MALDI-TOF mass spectrometers still leave much to be desired. For instance, the lower mass range up to about m/z=1000 daltons is masked by such a strong chemical background that it is not possible to evaluate the mass spectra. The background originates to a large extent from molecules of the matrix substance. When these are smashed by laser light pulses with the currently usual pulse durations and energy densities, they come together in the hot, but rapidly adiabatically cooling plasma of the desorption cloud to form complex ions of widely varying masses, so generating an almost continuous chemical background. It is therefore not possible to read the sequence of the first eight to ten terminal amino acids.

A special method for also reading the terminal sequences through metastable decay of a selected type of ISD fragment ion, as well as for a more detailed structural analysis of ISD fragment ions, consists in exploiting the instability of these fragment ions and measuring the granddaughter ions created by metastable decay, using a MALDI-TOF-TOF mass spectrometer equipped for recording ergodically generated fragment ions (D. Suckau and A. Resemann: DE 103 01 522 A1; GB 2 399 218 B; U.S. Pat. No. 7,396,686 B2). The method is, however, disadvantageous for large-scale protein sequencing because, after a first spectral evaluation, at least two further granddaughter ion spectra of c and z ISD fragment ions have to be acquired. In addition, an expensive MALDI-TOF-TOF mass spectrometer with a post-acceleration unit is needed in order to also acquire spectra of the fragment ions created by metastable decay.

In MALDI mass spectrometry, considerable skill is required in order to set the detector amplification and the MALDI conditions so as to optimally exploit the 8-bit range of the analog-to-digital converter (ADC) in the transient recorder, without either exceeding its dynamic measurement range (the "measurement window") of only 1:255 counts through oversaturation or failing to detect each of the ions that has been created as a result of a signal that is too weak. The impact of the ions on the secondary electron multiplier (SEM) only generates a small quantity of between zero and about six electrons; the numbers accord with a Poisson distribution. The Poisson distribution is characterized by having a standard deviation equal to its mean value; this means that there are always some ion impacts that do not generate secondary electrons (null events), and the number of these becomes larger as the mean value becomes smaller.

According to the prior art, the amplification of the SEM in a MALDI time-of-flight mass spectrometer is considered to be optimal if a single ion with a mass of about m/z=1000 daltons and an energy of around 30 kilo-electronvolts generates, on average, a signal of about 2.5 counts of the ADC in the transient recorder; the measuring range for ions in the measuring period of 0.5 or 0.25 nanoseconds is then 1:100, and the loss of signals from individual ions is negligibly small, at least in the mass range normally measured, which extends up to m/z=3000 daltons. As the ion signal usually extends over several measuring periods, there must not be more than a few hundred ions in an ion signal containing ions of the same mass if oversaturation is to be avoided. Adjusting the quantity of ions in this way has, however, the effect that the ions are no longer all detected in the higher mass range above three kilodaltons because more and more null events occur as the mass increases. The sensitivity of any SEM, i.e. the number of electrons generated in the maximum of the Poisson distribution, decreases with mass m at least by $1/\sqrt{m}$; for this reason sequencing is at present limited to a maximum of 70 amino acids at the C-terminus (about eight kilodaltons) and 50 amino acids at the N-terminus (around six kilodaltons). Optimal adjustment of the MALDI conditions calls for a great deal of knowledge about the effect of the laser light parameters on the MALDI processes.

Matrix assisted laser desorption uses (with a few exceptions) solid sample preparations on a sample support. The samples essentially consist of small crystals of the matrix substance mixed with a small proportion (only about one hundredth of one percent) of molecules of the analyte substances. The analyte molecules are individually incorporated in the crystal lattice of the matrix crystals, or are located at the boundaries between the crystals. The samples prepared in this way are exposed to short UV laser light pulses. The duration of the pulse is usually a few nanoseconds, and depends on the laser being used. This creates a vaporization plasma containing neutral molecules and also ions of the matrix substance along with a few analyte ions.

The nitrogen lasers normally used in the past are not suitable for high throughputs, since they only have a life time of a few million laser pulses. They are nowadays increasingly being replaced by solid-state lasers, whose life time is more than a thousand times greater. Solid-state lasers deliver a smooth energy density profile right across the laser spot provided by the lens system. The energy density profile approximately follows a Gaussian distribution.

The introduction of solid-state lasers into MALDI technology in place of the nitrogen lasers previously used led to the surprising discovery that the smooth beam profile from these solid-state lasers actually reduced the yield of ions. The profile of the beam from a nitrogen laser consists of micro-spots, whose position varies from one laser pulse to the next. For this reason, a method for profiling the laser beam from solid-state lasers to create a number of individual spots of optimum diameter was developed, and this increased the yield of ions even above the yield obtained from nitrogen lasers. This technology has become known under the name "Smart Beam", and is described in detail in DE 10 2004 044 196 A1; GB 2 421 352 A; U.S. Pat. No. 7,235,781 C1 (A. Haase et al.). This technology makes it possible to achieve an increase in the ion yield by optimizing the diameter and number of the laser spots. A favorable embodiment shows 4 to 30 spots with less than 10 micrometers in diameter each. It therefore provides a method where, by profiling the laser beam, a high yield of analyte ions can be achieved at the same time as optimal adaptation to the measuring window of the transient recorder.

Not every matrix substance can be used for non-ergodic ISD fragmentation. The matrix substance α-cyano-4-hydroxycinnamic acid (CHCA), which is extremely suitable for analyzing peptides by ergodic PSD fragmentation, yields hardly any ISD fragment ions. Until now, dihydroxybenzoic acid (DHB) has mainly been used as the matrix substance for ISD. It has recently become known that the yield of ISD fragment ions can be significantly increased through the use of suitable matrix substances that easily donate hydrogen radicals (K. Demeure et al.: "Rational Selection of the Optimum MALDI Matrix for Top-Down-Proteomics by In-Source Decay", Anal. Chem. A; Web Oct. 17, 2007). One such matrix substance is 1,5-diaminonaphthaline (1,5-DAN), but it can be expected that matrix substances that work even better will soon be available. These discoveries indicate that spontaneous, non-ergodic ISD fragmentation is primarily initiated by chemical reactions. These new matrix substances that readily donate hydrogen radicals are, moreover, able to open up the disulfide bridges in large proteins that lead to ring structures. Until now, the ring structures have prevented sequence decoding by ISD beyond the disulfide bridge, since fragmentation here results in split segments that still cohere across the ring structure. Opening of the disulfide bridges is caused in the basic environment of the plasma by the amino groups of the 1,5-DAN and by the donated hydrogen radicals.

Although the ISD method has been known for some 10 years, only recently has the progress been made that allows ISD to be applied easily. This progress is attributable, at least in part, to recent discoveries about the MALDI processes, but a great deal of research work is still required before the phenomena will be fully understood.

SUMMARY

In accordance with the principles of the invention, matrix substances favorable for spontaneous, non-ergodic fragmentation (ISD) are used in combination with short laser light pulses forming arrays of small diameter spots ("smart beam"). With this arrangement, first the yield of ISD fragment ions increases, second sample consumption is radically reduced, and third, most importantly and surprisingly, the background in the lower mass range of the mass spectrum is greatly reduced. Signals of monomer and dimer ions of the matrix substance clearly show up from the reduced background. When suitable matrix substances such as 1,5-DAN are irradiated with these short laser light pulses (with a duration of at most one nanosecond), an extraordinarily large number of spontaneous, non-ergodic ISD fragment ions is generated, from which, if all the MALDI parameters are optimally selected, at least the c fragment ions can be evaluated against the background, even in the lower mass range of the mass spectrum below 1000 dalton which was impossible hitherto. As the duration of the laser light pulse increases, the background also increases; for particularly suitable matrix substances it may even be possible to evaluate the results for laser light pulses with a duration of two or three nanoseconds.

The invention correspondingly provides a method for the acquisition of ISD fragment ion spectra that allows the sequence of amino acids in the range below 1000 dalton to be read. This method includes preparing the samples with suitable matrix substances and by irradiating the samples with short UV laser pulses with a maximum duration of three nanoseconds, preferably even shorter than one nanosecond. The UV laser beam should have a spatial profile of a multitude of small spots with diameters below ten micrometers. Series of individual spectra are added to a sum spectrum, as usual.

To include the measurement of higher ISD fragment ion masses into the series of spectrum acquisitions, the amplification of the secondary electron multiplier is initially set to a value sufficiently low that the signals of the ISD fragment ions can be effectively evaluated against the background, but over the course of the series of acquisitions of individual time-of-flight spectra from a sample, both the amplification of the SEM and the lower mass limit of the ion signals acquired in the individual time-of-flight spectra are gradually increased. As a result, the background ions are no longer recorded, but the ISD fragment ions of higher masses appear in the spectrum. The individual time-of-flight spectra are, as usual, added to form a sum time-of-flight spectrum. This spectrum can then be converted to a mass spectrum with the aid of the calibration curve.

The invention thus provides methods for large-scale, inexpensive sequence analysis of proteins by acquiring ISD daughter ion spectra in rather simply designed reflector time-of-flight mass spectrometers, permitting evaluation of the spectra from low masses near terminal amino acids up to very high masses of more than ten kilodaltons. The time-of-flight mass spectrometer need no longer contain the expensive equipment used for the acquisition of PSD fragment spectra. Instead, it need only contain a short-pulse UV laser with beam profiler and equipment for a delayed extraction of the ions (DE); preferred methods require an ion selector, in addition, located between the ion source and the ion detector, which can mask out light ions below an adjustable flight-time limit. A resolution of at least $R=m/\Delta m=20\,000$ should, however, be maintained in the mass range of about 10 kilodalton.

The lower mass limit for the recorded ion signals can be raised by starting digitization in the transient recorder later and later, but preferably by means of suppression of a progressively higher mass range of ions. This can be done in MALDI-TOF devices by a time-of-flight selector, and in MALDI-OTOF devices by adjusting the lower mass limit of the ion guide system between the ion source and the flight path.

In time-of-flight mass spectrometers with orthogonal ion injection (OTOF-MS), the method can be applied analogously, but in this case each recorded mass range is selected not by the ion selector but by an appropriately controlled ion guide system.

The method can be used, for instance, to perform diagnostic assays with which polymorphisms and post-translational modifications in selected, purified proteins can be detected very quickly. The assays can be equipped with small protein sequence databases, containing all the polymorphisms and all the post-translational modifications of these proteins. Commercially available protein identification programs can then very rapidly, and with little computation, establish the group to which each of the proteins under examination belongs.

BRIEF DESCRIPTION OF THE DRAWINGS

FIGS. 4 and 5 schematically illustrate the utilization of the ADC's measuring window in the transient recorder before and after application of this invention. The measuring window extends from a lower limit (20) with zero counts up to an upper limit (21) with 255 counts.

FIG. 4 illustrates the utilization of the measuring window before the method according to the invention is applied. The lower mass range up to about one kilodalton is fully occupied here with background signal (22). The mean value (24) of the c fragment ions and, particularly, their lower intensity variation limit (25) disappear from the measuring window in the higher mass range, limiting the ability to evaluate them. This applies in even greater measure to the mean value (27) and the lower variation limit (28) of the z fragment ions.

In FIG. 5, it can be seen that, after application of the invention, the background (22) has decreased sharply in comparison with the fragment ion signals. This is due to the short and beam-shaped UV laser light pulse and the favorable matrix substance; supported by the reduction in amplification. The mean value (24) of the c fragment ions and their variation limit (25) now extend up to higher masses. The same is true for the mean value (27) and the lower variation limit (28) of the z fragment ions.

DETAILED DESCRIPTION

Figure 1:
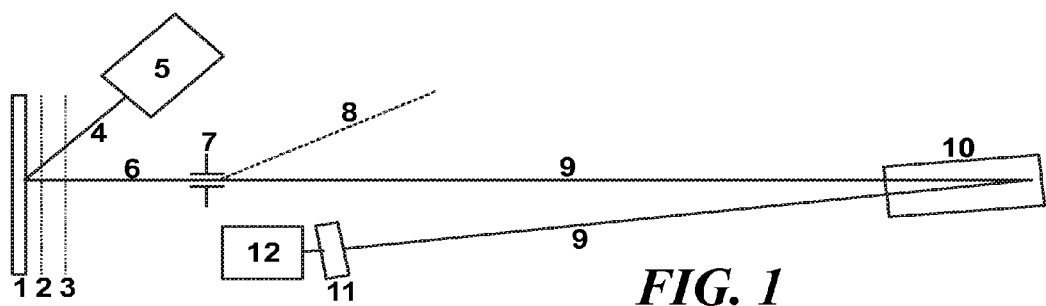
FIG. 1 shows schematically a simple, economically manufactured MALDI-TOF time-of-flight mass spectrometer that can be used for this invention. A large number of several hundred samples is located on the sample support plate (1) opposite the acceleration electrodes (2) and (3), and, by moving the sample support plate (1), the samples can be moved into the pattern of radiation spots of the beam-profiled laser light pulse (4) from the laser (5), where they are ionized. The ions, e.g. the ISD fragment ions, which are generated in pulses, are accelerated, after a short delay, by the acceleration electrodes (2) and (3) to form an ion beam (6) that must pass through the ion selector (7), and whose light ions, below a limiting time of flight, can be diverted as a separate beam (8). The remaining beam (9) of heavier ions is then reflected by the reflector (10) onto the secondary electron multiplier (11). The output current from the secondary electron multiplier is passed to the transient recorder (12), where it is converted into a series of digital measurements.

While the invention has been shown and described with reference to a number of embodiments thereof, it will be recognized by those skilled in the art that various changes in form and detail may be made herein without departing from the spirit and scope of the invention as defined by the appended claims.

The invention provides basically a method for the acquisition of ISD fragment ion spectra that allows the sequence of amino acids in the range below 1000 dalton to be read, which was not possible hitherto. In this method, the samples are prepared with suitable matrix substances like 1,5-DAN and by irradiating the samples with short UV laser pulses with a preferred maximum duration of one nanosecond. The UV laser beam should have a spatial profile with a multitude of small spots with diameters below ten micrometers each ("smart beam"). Series of individual spectra are added to a sum spectrum, as usual.

To extend the measurement towards higher ISD fragment ion masses, the method of the invention has to be modified. For the series of spectrum acquisitions from a sample, the amplification of the secondary electron multiplier is initially set, as above, to a value sufficiently low that the signals of the ISD fragment ions can be effectively evaluated against the background. Over the course of the continued series of acquisitions of individual time-of-flight spectra from the sample, however, both the amplification of the SEM and the lower mass limit of the ion signals acquired in the individual time-of-flight spectra are gradually increased. As a result, the background ions are no longer recorded, but the ISD fragment ions of higher masses appear in the spectrum. The individual time-of-flight spectra are, as usual, added to form a sum time-of-flight spectrum. This spectrum can then be converted to a mass spectrum with the aid of the calibration curve.

The invention thus includes an initial reduction in the amplification of the SEM by lowering the supply voltage before the series of mass spectra is taken from a sample. The objective is to adjust the amplification in such a way that all the signals of the ISD fragment ions can effectively and easily be evaluated against the background. It may be advantageous here if the output electron current from the SEM only falls within the measuring window of the ADC in the transient recorder when several ions, e.g. five or even ten, arrive at the SEM within the same measuring period. In this way, most of the ion signals from the chemical background are fully suppressed, and the ability to evaluate the mass spectra in this mass range is improved.

However, the low amplification of the SEM means that no ion signals are then registered at higher masses m, because the sensitivity of any SEM decreases roughly with $1/\sqrt{m}$ or even stronger. The method according to the invention therefore also consists in progressively raising the amplification of the secondary electron multiplier during the acquisition of a series of hundreds or thousands of individual time-of-flight spectra, while synchronously suppressing the ions below a progressively raised mass limit so that no further background is added in the lower mass range. The amplification of the SEM and the mass limit for suppressing light ions can be raised either in steps or continuously. The SEM should be amplified to a level which ensures that no ion signals are lost in the upper mass range extending to about 10 kilodaltons and above, provided the ions do release at least one secondary electron on impact. In this way a mass spectrum is obtained that can be efficiently evaluated from the terminal amino acids up to very high masses of 10 to 12 kilodaltons. The c fragment ions can be read up to around at least 80 amino acids, and the z fragment ions up to around 60 amino acids.

The invention can be implemented in various mass spectrometers; MALDI-TOF mass spectrometers with various levels of complexity, or alternatively MALDI-OTOF mass spectrometers can, in particular, be used. The use of other mass spectrometers is also possible, but is generally less advantageous, because of the fact that their mass ranges are restricted in comparison with time-of-flight mass spectrometers.

For a preferred method according to the invention, a relatively simple reflector time-of-flight mass spectrometer can be used, as illustrated schematically in FIG. 1. The simple TOF is apt for a high throughput, but without the ability to distinguish directly between leucine and isoleucine or between glutamine and lysine. The use of this simple time-of-flight mass spectrometer already provides methods for fast, inexpensive sequence analysis of purified proteins by acquiring their ISD daughter ion spectra with a wide mass range. Several thousands of proteins may be sequenced per day at low costs.

The simple time-of-flight mass spectrometer used here comprises, beside the electronics, the following subsidiary units:
a delayed extraction ion source for ionization by matrix assisted laser desorption, consisting of a sample support plate (1), two accelerating electrodes (2) and (3), and a laser (5), which supplies UV laser light pulses of at most three nanoseconds in duration, preferably with spatial beam profiling;
an ion selector (7) that can suppress light ions below a controllable time-of-flight limit;
a reflector (9) which, in combination with the delayed extraction in the ion source, can achieve a high mass resolving power, and
an ion detector consisting of a secondary electron multiplier (11) and a transient recorder (12).

Figure 6:
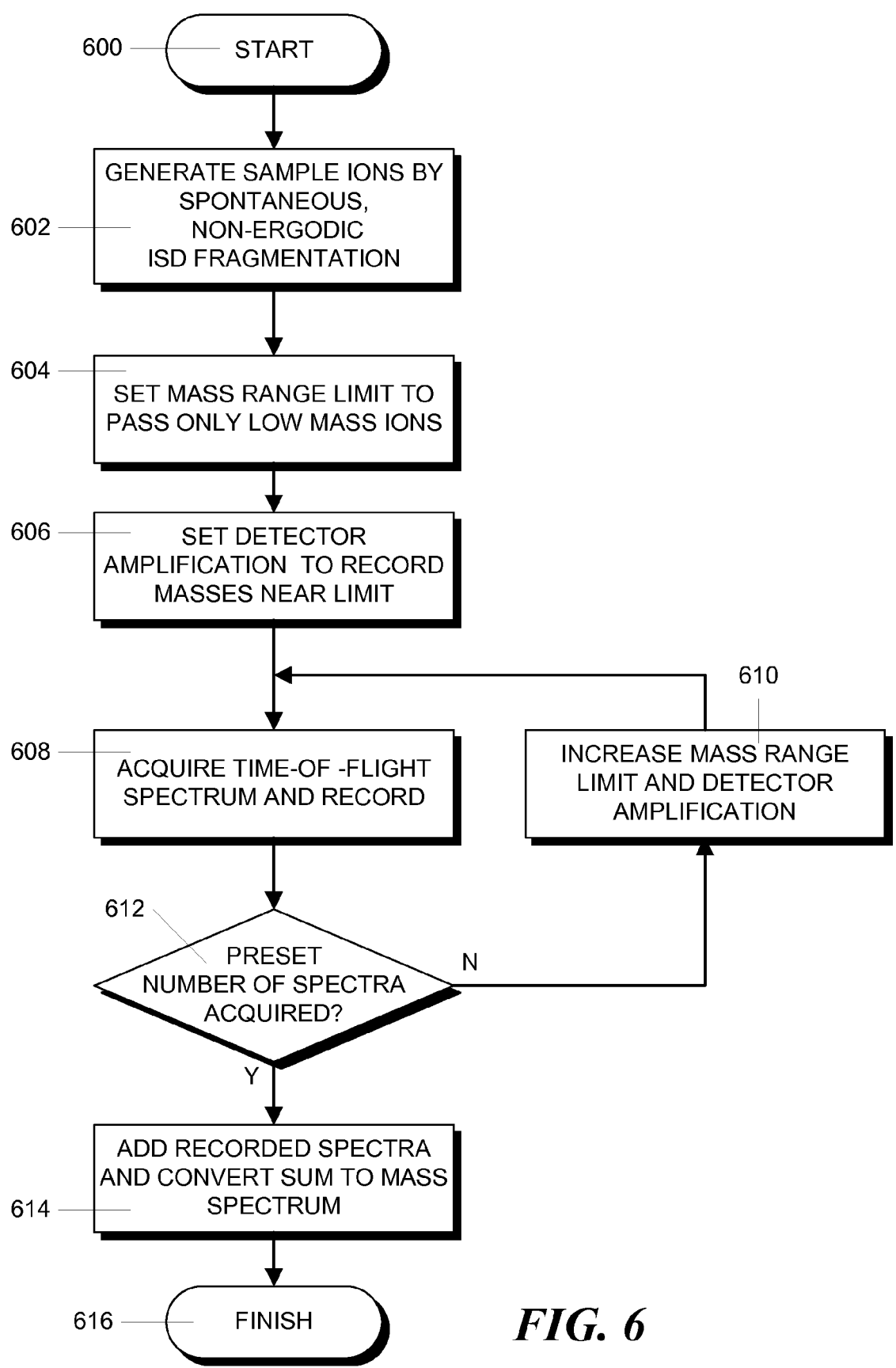
FIG. 6 is a flowchart showing the steps in an illustrative process for acquiring a mass spectrum in accordance with the invention.
Figure 7:
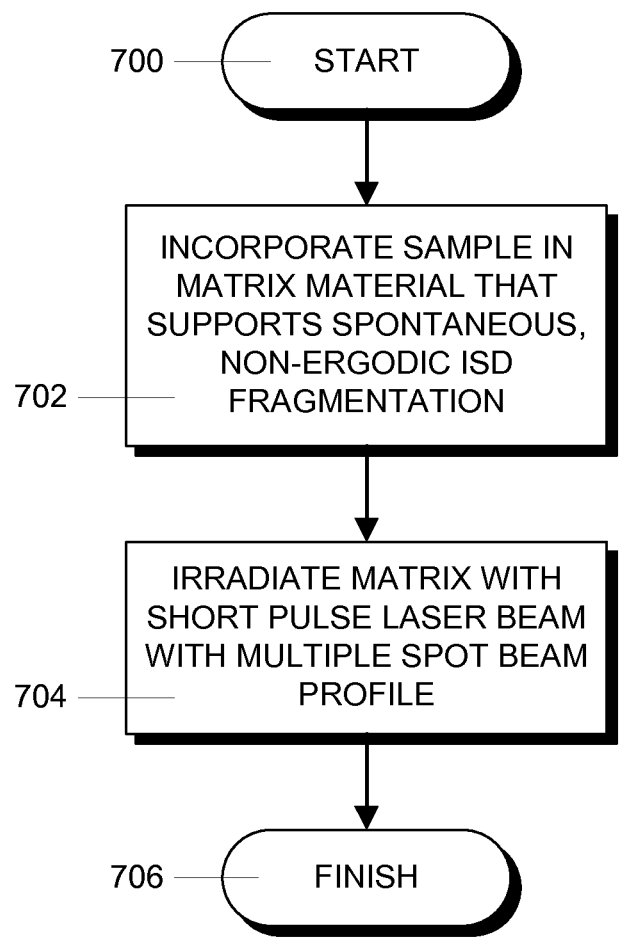
FIG. 7 is a flowchart showing the steps in an illustrative process for generating fragment ions by means of spontaneous, non-ergodic fragmentation (ISD).

A preferred method according to the invention for this mass spectrometer is shown in FIG. 6. This process starts in step 600 and proceeds to step 602 where sample ions are produced by spontaneous, non-ergodic ISD fragmentation. This step is shown in more detail in FIG. 7. The ion production process starts in step 700 and proceeds to step 702 where the sample is prepared on the sample support (1) with a matrix substance that chemically supports spontaneous, non-ergodic ISD fragmentation. In step 704, the production process involves irradiating the matrix thus prepared with short duration laser light pulses with a beam spatial profile formed by an array of small diameter spots. The ion production process then finishes in step 706.

In step 604, the low mass range limit of the mass spectrometer is set so that ions with the lowest masses of interest are analyzed by the mass spectrometer. Next, in step 606, the amplification of the secondary electron multiplier (11) is set to a low level such that the signals of all the ISD fragment ions stand out from the background. Then, in step 608, an individual time-of-flight spectrum is acquired and recorded or stored. In step 612, a determination is made whether a predetermined number of time-of-flight spectra have been acquired. If it is determined in step 612 that the predetermined number of spectra have not been acquired, the process proceeds to step 610 where the mass range limit and the detector amplification are increased.

Step 608 is then repeated. This process continues until a predetermined number of time-of-flight spectra have been acquired. Therefore, a series of individual time-of-flight spectra are acquired from one sample, each spectrum being initiated by a laser light pulse, and where both the amplification of the SEM and the time-of-flight limit of the ion selector that suppresses the light ions are progressively raised during the series of scans.

If, in step 612, it is determined that the predetermined number of spectra have been acquired, then the process proceeds to step 614 where the individual time-of-flight spectra of the acquisition series are added to form a sum time-of-flight spectrum in the usual way. The addition can immediately include all the sample's time-of-flight spectra, or it can be done in groups. The sum time-of-flight spectrum can then be converted into a mass spectrum with the aid of a calibration curve, also in the usual way. The process then finishes in step 616. From this mass spectrum, the ISD fragment ion signals can be used to determine the N-terminal and C-terminal sequences, in most cases from the terminal amino acids up to very high masses in each case. It is not, however, possible to distinguish between leucine and isoleucine, while glutamine and lysine can only be distinguished with high mass resolution and mass accuracy. If the mass spectrometer according to FIG. 1 has a scanning rate for ISD fragment ion spectra of two kilohertz, then about 10,000 individual time-of-flight spectra can be acquired within five seconds, of which preferably a few hundred are used for the lower mass range, and several thousand for the top mass range, in order to provide sufficient sensitivity there. The acquisition of 10,000 individual time-of-flight spectra from one sample is only made possible by the extremely low sample consumption of the short-pulse laser with beam profiling.

As has already been described above, several matrix substances that chemically support ISD fragmentation are known to those skilled in the art; these include, for instance, DHB (dihydroxybenzoic acid), and particularly 1,5-DAN (1,5-diaminonaphthaline), or, even better, mixtures of 1,5-DAN with PA (picolinic acid). It can be expected that further matrix substances will be found in the near future that contribute even better to ISD fragmentation. These matrix substances increase the yield of ISD fragment ions, allow the sequence to be read beyond locations where ring structures are formed by sulfide bridges, and, in combination with a short-pulse laser, lower the chemical background in the spectrum. The samples can, for instance, be prepared on sample support plates that have hydrophilic anchor sites for the sample droplets in a strongly hydrophobic surrounding. Commercially available sample support plates with the size of a standardized microtitre plate have, for instance, 384 hydrophilic anchor sites, each with a diameter of 0.8 millimeters. The sample support plate can be used in any automatic machine that can handle microtitre plates, such as pipetting machines.

The short-pulse laser is used in order to keep the chemical background in the lower mass range of the mass spectrum as low as possible so that, in combination with the matrix substances that support ISD, the mass spectrum can be evaluated right down to the terminal amino acids. For this reason, the laser light pulse should not be longer than at most three nanoseconds, and preferably only one nanosecond or even much less. The laser is preferably a solid-state short-pulse laser with beam profiling, as was described in the introduction.

The effect of the short UV laser pulse is not yet fully understood. It can be assumed, however, that within the first 500 picoseconds, the laser light couples to the solid material as a whole, not to the single molecules, heating up the material to a temperature far above the boiling point without transformation into a gas (boiling delay). Only then the transformation into the gaseous hot plasma of extremely high pressure happens, with a transformation surface shifting rapidly through the material. The internal energy of the molecules, even the matrix molecules, is only moderately increased. The plasma immediately starts to expand and cool adiabatically; up to here without much damage to the molecules. Only if the laser pulse continues, the molecules can take up much more energy, particularly the matrix molecules, forming the chemical background. Within the hot plasma, all types of chemical reactions occur easily, such like proton transfer to the larger molecules, ionizing them, and effects of hydrogen radicals, fragmenting them.

A key element of the invention consists in lowering the amplification of the SEM by reducing its supply voltage at the beginning of a series of scans. Due to the high-resistivity coating, a few milliseconds are required to adjust the surface voltages within the SEM; it is therefore not possible to increase the amplification of an SEM during the acquisition of a single time-of-flight spectrum, a process that lasts only about 100 to 200 microseconds. The aim is to set an amplification that optimizes the ratio of ISD fragment ion signals to the background noise. For this, it is advantageous if the output electron current only falls within the conversion range of the transient recorder when more than one ion (at least two) reaches the SEM during the same measuring period. It is possible, for instance, to select the amplification so that at least five, or even ten, ions must arrive within the same measuring period in order to create a count of the ADC (analog-to-digital converter) in the transient recorder. In this way, most of the ion signals from the chemical background are suppressed, and the ability to evaluate the mass spectra in this mass range is improved. By adjusting the laser energy, and by distributing the laser radiation between a sufficient number of radiation spots, each with sufficient power density, it is possible to ensure that sufficiently strong signals are registered for all the z fragment ions in this mass range. Since the signals from the c fragment ions are stronger by a factor of about ten, these are also reliably registered.

However, the low amplification of the SEM means that no ion signals are then registered at higher masses. The method according to the invention therefore also provides a progressive increase of the amplification of the secondary electron multiplier during the acquisition of a series of individual time-of-flight spectra, while synchronously suppressing the ions in a larger and larger range of lower masses from being recorded. In the case of the mass spectrometer according to FIG. 1, this can be done with the ion selector (7) between the ion source (1, 2, 3) and the ion detector (11). The ion selector (7) can, for instance, be a deflection capacitor that only allows ions to pass if voltage is removed at a certain time of flight. In this way, light ions with a short time of flight below an adjustable flight time limit can be suppressed by the ion selector (7) by diverting a beam (8). The amplification of the SEM (11) and the mass range that is suppressed can be increased either in steps or continuously. The amplification of the SEM should finally reach such high levels that no ion signals are lost in the upper mass range extending to about 10 kilodaltons, provided the ions do release at least one secondary electron. The ongoing addition of the individual time-of-flight spectra then yields a mass spectrum that can be efficiently evaluated from the terminal amino acids up to very high masses of at least 10 kilodaltons. Raising the SEM amplification in this way can ensure that the c fragment ions generally have a sufficiently high intensity over the entire mass range, until more and more statistically distributed gaps occur by overwhelming numbers of null-events. Similar considerations apply to the z fragment ions, although their intensities are lower than those of the c fragment ions by a factor of between five and ten. The c fragment ions can be read up to around 80 amino acids, and the z fragment ions up to around 60 amino acids.

If an even simpler mass spectrometer with no time-of-flight selector is used, then the lower mass range can also be suppressed to be recorded by simply delaying the start of digitization or storage in the transient recorder until increasingly high ion masses, i.e. later flight times, are reached. This solution, which entails controlling the point at which the digitization or storage begins, is not, however, preferred here, since the lifetime of the detector is reduced by the heavy overload with ions of low mass that are not suppressed when the amplification is high.

The mass spectrum then shows the c fragment ions in an almost uniformly intense series of signals, since all the amino acids, with the exception of proline, cleave with about the same ease. The amino acids can be determined from the spacings in the known way; only leucine and isoleucine are indistinguishable, while glutamine and lysine can only be differentiated with difficulty, and with the aid of a mass spectrometer with extremely high mass accuracy. The gap that results from proline's failure to cleave can be closed through the knowledge that proline plus another amino acid must fit here. The principle of this ISD method has been known to those skilled in the art for some years; the achievable quality of the mass spectra, however, has risen in the meantime to very much higher levels.

FIGS. 4 and 5 give a schematic impression of how the utilization of the intensity measuring window (or of the dynamic measuring range) of the analog-to-digital converter (ADC) in the transient recorder along the mass scale is changed by the invention. In addition to the occurrence of background (22), the mean value curves (24) and (27) of the c and z fragment ions, and their respective upper and lower limits (23, 25) and (26, 28) are indicated for the variations in the intensities, both before (FIG. 4) and after (FIG. 5) application of the invention.

The term "transient recorder", which has become accepted with reference to time-of-flight mass spectrometers, should not, however, be understood here too narrowly. It should be taken to mean any arrangement that amplifies the output current from the SEM, digitizes it and saves the digital values in such a way that the time-of-flight spectrum can be extracted from it. The arrangement should preferably also be able to perform addition of the time-of-flight spectra in real time. If the arrangement allows the digitization or storage of the digital values to be started with a controllable delay in relation to the commencement of ion acceleration, then this arrangement can also be used to suppress the ion signals from the lower mass range.

In many assays, the inability to distinguish between leucine and isoleucine or glutamine and lysine is acceptable, since polymorphisms in which leucine and isoleucine are exchanged, or in which glutamine and lysine are exchanged, are relatively rare, and can often be replaced by other polymorphisms for the purpose of the diagnosis. The simple time-of-flight mass spectrometer of FIG. 1 can then be used to perform assays for large-scale identification of polymorphisms or modifications. In a benchtop device with a footprint of 40 by 60 centimeters and a height of one and a half meters, the mass spectra of 384 protein samples on a sample support plate, each being composed of 10,000 individual time-of-flight spectra, can be measured automatically in the time of about half an hour. If a small sequence database containing all the forms of polymorphisms and modifications of the protein being examined is available, then at the end of this half-hour, all the groupings of the protein samples will be known. Search programs are commercially available for this task. Automatic machines are already available for preparing the protein samples, usually on the basis of immobilized antibodies in suitable extraction tubes. These machines can extract and purify a few dozen different proteins from body fluids in parallel. Larger proteins containing more than about 140 amino acids can be split with suitable enzymes.

In addition to the protein analyses described above for determining genetic intolerances and predispositions to disease, and also for establishing the modification statuses of individual amino acids, there are many other fields of application, such as the identification of a type of meat (beef, gazelle or kangaroo?) or its country of origin, and possibly even the specific farm. In a similar way to the SNPs (single nucleotide polymorphisms) of DNA, the polymorphisms (or modification statuses) of proteins can be used to identify the ancestry of living organisms. For all of these questions, remarkably inexpensive assays can be developed. In addition to hundreds of such routine applications, many other problems in current protein research can be solved.

Figure 2:
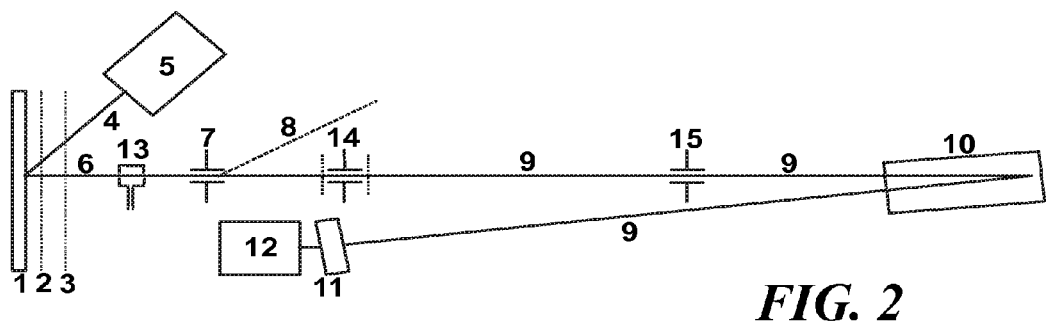
FIG. 2 illustrates schematically a much more elaborate MALDI-TOF-TOF time-of-flight mass spectrometer that is also able to record mass spectra of fragment ions that can be created and measured either by collision-induced decomposition (CID) in the gas cell (13), or by increased internal energy of the analyte ions produced by excitement with longer laser light pulses (PSD=post-source decomposition), with ergodic decomposition and post-acceleration in the post-acceleration unit (14). Those parent ions that have not decayed can be suppressed by the parent-ion suppression unit (15). The leucine/isoleucine and glutamine/lysine pairs can also be distinguished with this mass spectrometer, as they yield slightly different CID and PSD daughter ion spectra.

If, however, the purpose of the analysis also requires an unambiguous distinction between the amino acids leucine, isoleucine, glutamine and lysine, then methods for more precise determination can also be applied. Biochemical methods, for instance, can be used in order to chemically mark the amino acids in question before they undergo mass spectrometric analysis. They can also be differentiated by mass spectrometric methods, although a more elaborate MALDI-TOF-TOF time-of-flight mass spectrometer in accordance with FIG. 2 is needed. In this case, selected ISD daughter ions are excited to ergodic decay by collisions in the collision cell (13) or by longer laser light pulses; they are then selected in the ion selector (7), accelerated in the post-acceleration unit (14), and then measured, in the usual way, as granddaughter ion spectra. A comparison between a collision-induced dissociation (CID) spectrum and a laser-induced ergodic decomposition (PSD) spectrum shows differences between leucine and isoleucine, and also between glutamine and lysine. This more detailed analysis is also made possible by the fact that sample consumption for the first ISD analysis of the protein sequence is extraordinarily low, even though very large numbers of individual time-of-flight spectra have to be acquired.

Figure 3:
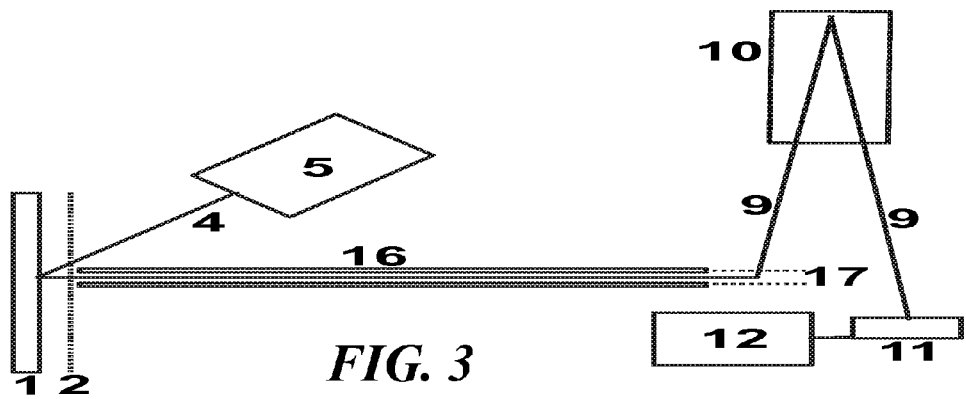
FIG. 3 schematically shows a MALDI-OTOF time-of-flight mass spectrometer in which the ions from the plasma cloud generated by the laser are guided by an ion guide system (16) to an ion pulser (17). The pulser (17) accelerates the ion beam (9) into the flight path of the OTOF, where a reflector (10) reflects the ions onto the detector (11). The RF ion guide system (16), which is implemented here as a multipole rod system, can be used to filter out ions with less than a limiting mass.

The method according to the invention can also be carried out in a time-of-flight mass spectrometer with orthogonal ion injection (OTOF-MS), as illustrated in the schematic diagram of FIG. 3. In order to select the mass range, which is changed along with the amplification of the SEM, such mass spectrometers have an ion guide system (16) that guides the ions from the ion source to the ion pulser (17) at the beginning of the flight path. Ion guide systems are usually implemented as RF multipole systems. These have a mass range characterized by a sharp mass limit at the bottom, and by a gradually attenuating mass range at the top. The lower mass limit is determined by the stability range of the Matthieu differential equations, while the upper limit is determined by the focusing of the pseudopotential, which becomes weaker and weaker until it can no longer overcome the Coulomb repulsion of the ions. The lower and upper mass boundaries differ by a factor of about 20. It is therefore possible, for instance, to first measure the ions in the mass range from 50 to 2000 daltons and then to raise the range, either gradually or in steps, by increasing the RF voltages at the ion guide system (16), thus cutting off the lower range up to a mass of 1000 daltons.

It is particularly important for the use of a MALDI-OTOF MS to use a short-pulse laser with a pulse length that is, if possible, no longer than one nanosecond. This generates relatively stable ISD fragment ions, since it is only irradiation of the ions after the first nanosecond that increases their internal energy and thereby leads to instability. This is important, as otherwise the spontaneous ISD fragment ions in the ion guide system (16), where they may remain for several milliseconds, will decay and appear in the mass spectrum. The mixture of ISD fragment ions and their granddaughter ions generated by ergodic decay cannot, however, be disentangled.

Those skilled in the art of mass spectroscopy can, with a knowledge of this invention, develop further analytic methods for refined investigations, for instance for the investigation of post-translational modifications and their structures.

What is claimed is:

1. A method for sequence analysis of proteins by acquiring mass spectra of spontaneous, non-ergodic fragment ions (ISD ions) from a protein sample in a mass spectrometer that ionizes the sample by matrix assisted laser desorption and that has an ion detector with a secondary electron multiplier having an amplification, the method comprising:
   (a) preparing a matrix including the protein sample and a matrix substance that supports spontaneous, non-ergodic fragmentation;
   (b) initially adjusting the mass spectrometer so that only sample ions with masses at or above a mass range limit are analyzed, the mass range limit corresponding to a mass of the terminal amino acids of the proteins;
   (c) initially adjusting the amplification of the secondary electron multiplier so that a spontaneous, non-ergodic ISD fragment ion spectrum can be detected above chemical background noise for sample ions with masses at the mass range limit;
   (d) irradiating the matrix with UV laser pulses to produce sample ions, each pulse having a maximum duration of one nanosecond and being formed by a plurality of distinct spots, each spot having a diameter below one micrometer;
   (e) acquiring an individual time-of-flight mass spectrum from sample ions;
   (f) after step (e), increasing the amplification of the secondary electron multiplier;
   (g) after step (e), increasing the mass range limit;
   (h) repeating steps (d)-(g) for a predetermined number of times; and
   (i) adding-up the individual time-of-flight spectra to form a sum spectrum.

2. The method of claim 1, wherein the matrix substance comprises 1,5-diaminonaphtalene.

3. The method of claim 1, wherein the value in step (h) is about 1,000 Daltons.

4. A method for sequence analysis of proteins in a sample by acquiring mass spectra of spontaneous, non-ergodic fragment sample ions (ISD ions) in a mass spectrometer with a matrix assisted laser desorption ion source and an ion detector with a secondary electron multiplier having an amplification, the method comprising:
   (a) using in the ion source a matrix containing the sample and a matrix substance that supports spontaneous, non-ergodic ISD fragmentation, and a laser that delivers laser light pulses to the matrix;
   (b) adjusting the mass spectrometer so that only sample ions with masses at or above a mass range limit are analyzed;
   (c) adjusting the amplification of the secondary electron multiplier so that ISD fragment ion signals can be measured above a chemical background for ions with masses near the mass range limit, and
   (d) acquiring a plurality of individual time-of-flight mass spectra from the matrix, each spectrum corresponding to one of said laser light pulses, while progressively increasing both the amplification of the secondary electron multiplier and the mass range limit of ions used to acquire the individual time-of-flight spectra between each spectrum acquisition.

5. The method of claim 4, wherein the mass spectrometer further includes a transient recorder that receives fragment ion signals and records the signals and wherein steps (b) and (d) comprise adjusting a point in time at which signal recordation in the transient recorder begins.

6. The method of claim 4, wherein the mass spectrometer comprises a MALDI-TOF mass spectrometer with axial ion injection containing an ion selector and wherein steps (b) and (d) comprise adjusting the ion selector so that only sample ions with masses at or above a mass range limit are analyzed.

7. The method of claim 4, wherein the mass spectrometer comprises a MALDI-OTOF mass spectrometer with orthogonal ion injection having an ion guide system with voltages that control the mass of ions passing therethrough, and wherein steps (b) and (d) comprise controlling the voltages in the ion guide system so that only sample ions with masses at or above a mass range limit are analyzed.

8. The method of claim 4, further comprising adding together the individual time-of-flight spectra acquired in step (d) to form a sum time-of-flight spectrum and converting the sum time-of-flight spectrum into a mass spectrum.

9. The method of claim 4, wherein the mass spectrometer further includes a transient recorder that records signals from the secondary electron multiplier and wherein, prior to step (d), the amplification of the secondary electron multiplier is set to a level such that the transient recorder records only signals produced by a plurality of ions arriving at the ion detector during a detection time period.

10. The method of claim 4, wherein each laser light pulse has a maximum pulse duration of three nanoseconds.

11. The method of claim 4, wherein each laser light pulse has a maximum pulse duration of less than or equal to one nanosecond.

12. The method of claim 10, wherein the laser is a solid-state laser having a beam shaping unit that produces a light beam spatial profile comprised of a plurality of spots.

13. A method for acquiring a mass spectrum from which polymorphisms and post-translational modification states in proteins in a sample can be detected with a mass spectrometer having a matrix assisted laser desorption ion source and an ion detector with a secondary electron multiplier having an amplification, the method comprising:
   (a) using in the ion source a matrix containing the sample and a matrix substance that supports spontaneous, non-ergodic ISD fragmentation;
   (b) irradiating the matrix with a pulsed laser beam having pulses of duration less than or equal to one nanosecond and a beam spatial profile consisting of a plurality of spatially separated spots;
   (c) adjusting the mass spectrometer so that only sample ions with masses at or above a mass range limit are analyzed;
   (d) adjusting the amplification of the secondary electron multiplier so that ISD fragment ion signals can be measured above a chemical background for ions with masses near the mass range limit,
   (e) acquiring a plurality of individual time-of-flight mass spectra from the matrix, each spectrum corresponding to one of said laser light pulses, while progressively increasing both the amplification of the secondary electron multiplier and the mass range limit of ions used to acquire the individual time-of-flight spectra between each spectrum acquisition; and
   (f) adding together the individual time-of-flight spectra acquired in step (e) to form a sum time-of-flight spectrum and converting the sum time-of-flight spectrum into the mass spectrum.

* * * * *